United States Patent [19]

Steichen et al.

[11] Patent Number: 4,745,794

[45] Date of Patent: May 24, 1988

[54] ANALYZER FOR CARBON DIOXIDE IN BEVERAGES

[75] Inventors: John C. Steichen, Landenberg, Pa.; James R. Small, Hockessin, Del.

[73] Assignee: E. I. Du Pont de Nemours and Company, Wilmington, Del.

[21] Appl. No.: 944,351

[22] Filed: Dec. 22, 1986

[51] Int. Cl.[4] .................. G01N 33/14; G01N 7/14
[52] U.S. Cl. .................................................. 73/19
[58] Field of Search .......................................... 73/19

[56] References Cited

U.S. PATENT DOCUMENTS

| | | | |
|---|---|---|---|
| 3,077,765 | 2/1963 | Dijkema | 73/19 |
| 3,673,853 | 7/1972 | Griswold et al. | 73/19 |
| 4,083,225 | 4/1978 | Day et al. | 73/19 |
| 4,120,192 | 10/1978 | Williamson | 73/19 |
| 4,150,560 | 4/1979 | Wieland | 73/19 |
| 4,179,918 | 12/1979 | van Strien | 73/19 |
| 4,373,374 | 2/1983 | Bajard | 73/19 |
| 4,461,165 | 7/1984 | Kesson | 73/19 |
| 4,550,590 | 11/1985 | Kesson | 73/19 |
| 4,607,342 | 8/1986 | Seiden et al. | 73/19 X |
| 4,673,927 | 6/1987 | Cianciavicchia et al. | 73/19 X |

Primary Examiner—Tom Noland
Attorney, Agent, or Firm—Hilmar L. Fricke

[57] ABSTRACT

An analyzer typically used in conjunction with a standard carbonated beverage container filling line that determines the concentration of a dissolved gas such as carbon dioxide of a beverage liquid being supplied to the filling line has the following components:

a. a sealed cell having an entry and an exit for liquids and a pressure transducer for measuring the pressure and a temperature transducer for measuring the temperature of the contents of the cell;

b. a first valve for diverting a portion of the liquid being supplied to the entry of the cell and a second valve sealing the exit of the cell to prevent the liquid from escaping;

c. a third valve for venting pressure from the cell;

d. an ultrasonic exciter attached to the cell that agitates the liquid in the cell and brings the liquid and the dissolved gas into equilibrium conditions;

e. a computer is used for sequencing the operation of the analyzer by opening the first valve to allow liquid to enter the cell and opening the second valve to allow liquid to leave the cell and then closing the first and second valve to retain liquid in the cell and opening and closing the third valve to reduce pressure in the cell and then engaging the ultrasonic exciter;

f. the computer receives a signal from the pressure and temperature measuring transducers and converts these signals to dissolved gas content in the liquid.

13 Claims, 2 Drawing Sheets

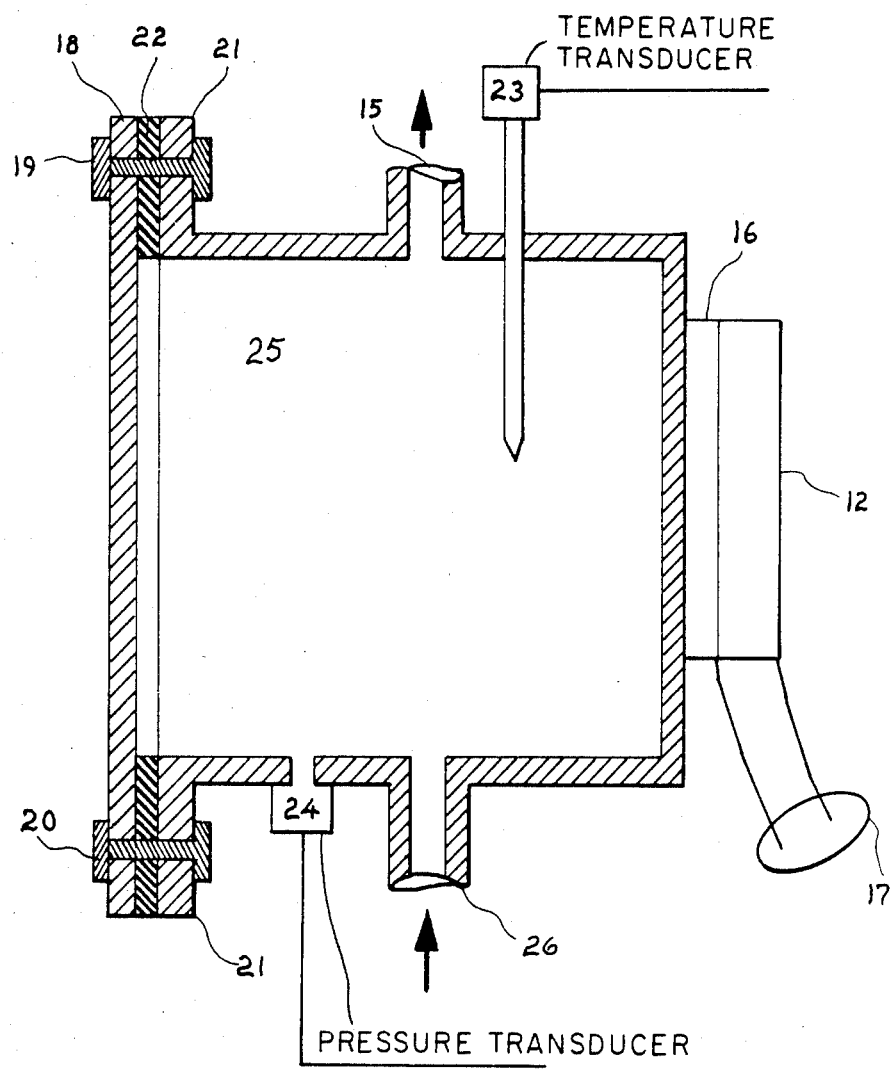

ANALYZER FOR CARBON DIOXIDE IN BEVERAGES

BACKGROUND OF THE INVENTION

This invention relates to an apparatus for analyzing the carbon dioxide content of liquids and in particular, an apparatus for measuring the carbon dioxide content of carbonated soda water beverages.

In a sealed container such as a can or a bottle, a carbonated liquid beverage comes to equilibrium with the gas phase above the liquid and the equilibrium pressure is directly related to the carbon dioxide content of the liquid. The exact mathematical relationship between the carbon dioxide content of the liquid and the temperature and pressure of the container and its contents depends upon the acidity and other chemical properties of the beverage. These relationships have been determined empirically and carbon dioxide content of a beverage can be determined by measuring the pressure in the container. However, in a typical high speed bottling or canning line which run at hundreds of cans a minute, a procedure in which a container is removed and then gas pressure is measured would allow many containers to be filled before an adjustment could be made for the carbonation level of the beverage. There is a need to rapidly measure the beverage before it is bottled or canned so that adjustments to the carbonation level can be made if necessary.

The carbonated beverage can be analyzed by removing a sample from the filling line and placing the beverage sample in a sealed container and allowing the beverage to come to equilibrium with the carbon dioxide gas. This usually requires several hours.

Prior techniques have been used to analyze samples such as shown in U.S. Pat. No. 3,077,765 issued Feb. 19, 1963 to Dijkema in which a sample of a beverage is removed and placed in a sealed container and the container is vibrated to bring the beverage into equilibrium with the carbon dioxide gas and the temperature of the beverage and gas and the pressure of the gas were determined. However, this method proved too slow and inaccurate since the amount of vibration needed to bring the gas and liquid to a state of equilibrium could not be accurately determined and changed with different beverages.

In U.S. Pat. No. 4,083,225 issued April 11, 1978 to Day et al, an ultrasonic transducer was placed in a beverage line and measured the quantity of gas bubbles in the beverage and determined carbon dioxide content from this measurement. This method also was inaccurate.

In U.S. Pat. Nos. 4,550,590 issued Nov. 5, 1985 and 4,461,165 issued July 24, 1984 both to Kesson show a method and apparatus for measuring and monitoring the gas in a liquid by placing a semipermeable membrane across the face of a chamber containing liquid. Gas from the liquid permeates through the membrane into a chamber and the pressure within the chamber is measured. U.S. Pat. No. 4,179,918 issued Dec. 25,1979 to van Strien shows a method of measuring the carbon dioxide content of beer by placing beer in a vessel and electrically measuring the pressure of the carbon dioxide atmosphere above the beer.

None of these prior art methods provide a rapid and accurate method for continuously monitoring the carbon dioxide content of beverages such as carbonated soft drinks.

SUMMARY OF THE INVENTION

An analyzer typically used in conjunction with a standard carbonated beverage container filling line that determines the concentration of a dissolved gas in a liquid such as the concentration of carbon dioxide of a beverage being supplied to the filling line having the following:

a. a sealed cell having an entry for liquids and an exit for liquids and means for measuring the pressure of the gas phase and means for measuring the temperature of the contents of the cell;

b. a first valving means for diverting a portion of the liquid being supplied for example to the filling line to the entry of the cell and a second valving means sealing the exit of the cell to prevent the liquid from escaping;

c. a third valving means for venting pressure from the cell;

d. an ultrasonic exciter attached to the cell capable of agitating the liquid in the container and in a short time bringing the liquid and the dissolved gas for example, carbon dioxide, into equilibrium conditions;

e. means for sequencing the operation of the analyzer by opening the first valve means to allow liquid to enter the cell, opening the second valving means to allow any residual liquid to leave the cell, closing the first and second valving means to retain liquid in the cell and then opening and closing the third valving means to reduce pressure in the cell and then engaging the ultrasonic exciter for a sufficient period of time to bring the dissolved gas for example, carbon dioxide, into equilibrium with the liquid and then measuring the pressure of the gas and the temperature of the liquid;

f. a computer which receives a signal from the means for measuring pressure and the means for measuring temperature and converts these signals to provide the dissolved gas content in the liquid.

BRIEF DESCRIPTION OF THE DRAWINGS

FIG. 2 shows a cross section of the cell used in the analyzer.

DETAILED DESCRIPTION OF THE INVENTION

Figure 1:
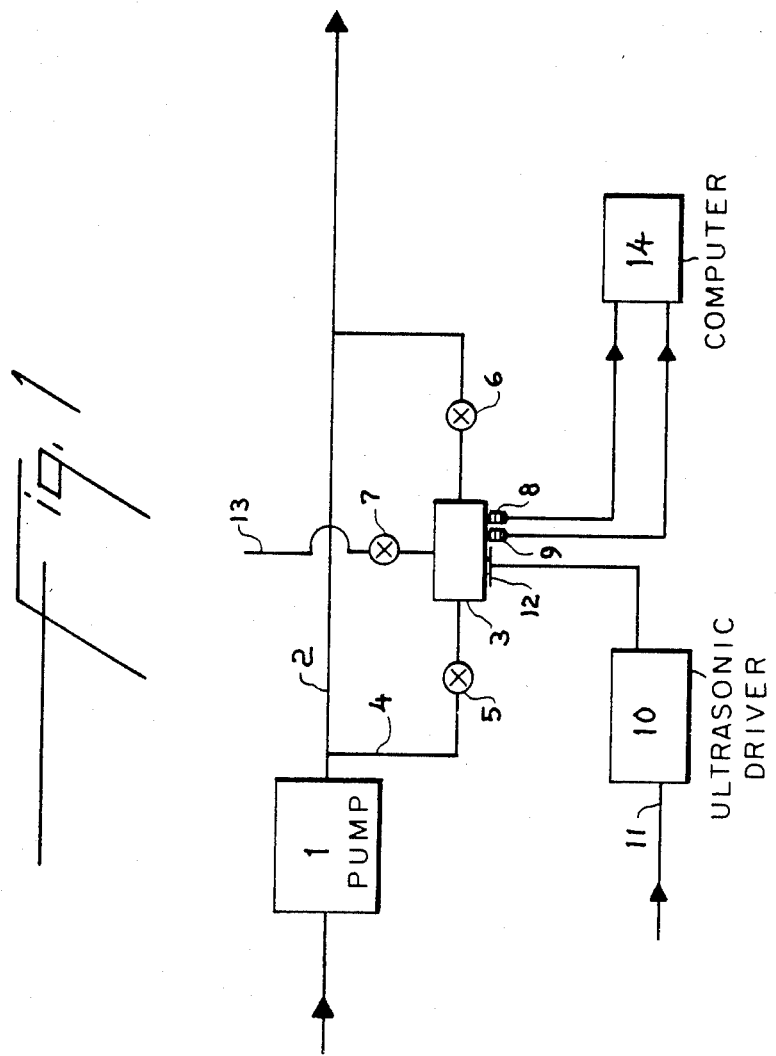
FIG. 1 shows a schematic diagram of the analyzer of this invention.

This invention is directed to an analyzer that is is used to determine the carbon dioxide content of beverages and in particular the carbon dioxide content of carbonated soft drinks and in particular sugar free beverages or beverages that contain an artificial sweetener. Preferably, the analyzer is used in conjunction with a standard filling line in which the carbon dioxide content of the beverage is measured before the can or bottle is filled.

FIG. 1 which is a schematic diagram of the analyzer shows pump 1 which pumps a carbonated beverage through line 2 to a conventional bottle or can filling line. A small sample of carbonated beverage is removed from the line 2 through sample loop 4 which feeds the sample into cell 3. In the sample loop 4, valves 5 and 6 are opened and sample flows from the line 2 to the cell 3. Periodically, valves 5 and 6 are closed, then valve 7 is opened briefly to vent to the atmosphere. The length of the sample loop 4 from the line 2 to the cell 3 is important to prevent cavitation and bubble formation in the cell 3. Either the length of the sample line from the cell 3 through valve 6 should be about 1/10 of the sample loop from the cell 3 through valve 5 to the filling line 2 or a flow restrictor should be used in this part of the loop. This will assure that the pressure in the cell 3 will be kept close to the pump 1 exhaust pressure.

Valves 5, 6 and 7 typically are solenoid valves manufactured by Parker Hannifin Corporation, Model 04F2X43X18ABFG005002, operated by air pressure and electricity at 120 volts AC and 0.085 amperes. An ultrasonic exciter 12, typically a 55 watt piezoelectric transducer made of lead zirconate titanate by Sonic Systems, Inc., of Newtown, Pa., and designed to operate in the frequency range of 38 to 42 kilohertz, is attached to cell 3 and driven by an ultrasonic driver 10, a variable frequency, 50 watt, solid state, push-pull, crystal controlled, Class C, power oscillator, typically operated at 120 volts AC and 0.5 amperes, also manufactured by Sonic Systems, Inc., of Newtown, Pa. An electronic strain gauge pressure transducer 8, typically manufactured by Data Instruments Inc., Model AK100 PSIS, providing an output signal of 1 to 5 volts DC when used in conjunction with sender Model MGW-10, manufactured by the Schurtermann & Benninghoven GmbH of Hilden, West Germany, over a pressure range of 0 to 100 PSIG with an accuracy of 1% full scale, is attached to the cell 3 to measure the pressure of the carbon dioxide gas when equilibrium condition is reached. A temperature transducer 9, typically manufactured by Schurtermann & Benninghoven GmbH, Model 7124-1-T-1/8-150-G-1980-A, employing platinum resistance sensor with an accuracy of +0.5° C. over the range of 0° to 50° C. when powdered with a Model MGW-21 sender of the same company and providing an output signal of 1 to 5 volts DC, is attached to the cell 3 to measure the temperature of the liquid and carbon dioxide gas in the cell 3 when equilibrium conditions are reached.

The following three steps are followed for measuring the carbon dioxide content of a beverage:

Step 1: Valves 5 and 6 of the sample loop are opened and valve 7 to the drain is closed. Beverage flows through the cell 3 and any residual sample and carbon dioxide gas that may be left in the cell is flushed out. The temperature of the cell comes to equilibrium with the temperature of the beverage of the filling line. The cell pressure is the pressure of the filling system.

Step 2: Valves 5 and 6 of the sample loop are closed thereby trapping beverage at the pressure of the system in the cell 3. For a very brief period, i.e., less than several seconds, valve 7 to the drain 13 is opened to allow the cell to depressurize to a pressure below the equilibrium pressure of the beverage, usually to atmospheric pressure. All valves are closed at the end of this step.

Step 3: The ultrasonic driver 10 activates the ultrasonic exciter 12 attached to the cell. This causes the pressure in the chamber to rapidly rise to the equilibrium pressure of the beverage. After the excitation period which is between several seconds and several minutes depending on the beverage, the temperature and pressure of the cell are measured via pressure and temperature transducers 8 and 9 and fed to the computer 14, preferably a calculating controller, and the carbon dioxide content of the beverage is calculated by a computer which receives the above measurements and bases its calculations on cell volume and an empirical formula.

The computer 14 preferably is a calculating controller, typically employing an 8085 microprocessor and an 8155 input/output device, is used to control the timing sequence of opening and closing the valves and actuating the ultrasonic driver. The microprocessor receives the pressure and temperature measurement signals from the cell and converts these signals to carbon dioxide content of the beverage. The carbon dioxide content can be displayed by the microcomputer or provided as an electrical signal to another instrument controlling the carbon dioxide content of the beverage.

FIG. 2 shows a cross section of the cell 3 used in the analyzer. The chamber 25 is cylindrical and holds a given volume of beverage to be analyzed and has an inlet 26 and an outlet 15. Beverage flow into the chamber 25 through the inlet and exits the chamber through the outlet. Welded to one end of the chamber is a flat plate 16 and an ultrasonic exciter 12, typically a piezoelectric lead zirconate titanate crystal, is attached thereto that is actuated by a signal 17 from an ultrasonic driver. The opposite end of the chamber is closed with a flat plate 18 that is bolted with bolts 19 and 20 to the flange 21 of the chamber and sealed with a rubber gasket 22 positioned and sealed in the chamber are the following: a temperature transducer 23, typically a platinum resistance sensor, for measuring the temperature of the beverage and a pressure transducer 24, typically an electronic strain gauge, for measuring the pressure of the carbon dioxide gas.

The following empirical formula is used to calculate the volume of carbon dioxide per volume of liquid:

$$V = \frac{4.33(P + 14.9)}{(T + 5.6)}$$

where
V is the volume of carbon dioxide per volume of liquid,
T is the temperature in Fahrenheit, and
P is the carbon dioxide pressure in PSIG (pounds per square inch gauge).

The carbon dioxide analyzer provides the operators of beverage bottling plants with the ability to continuously monitor the degree of carbonation of their products. The analyzer signal may be used to record the carbon dioxide content, or, additionally, to control the level of carbonation. Excess carbonation is undesirable because it can deform or cause failure of the beverage containers. Insufficient carbon dioxide levels may cause the beverage product to be undesirable to the beverage consumers. Also, operators of plants employing blending devices based on photometric analyzers require a measurement of carbon dioxide content since the optical properties of beverages are somewhat dependent upon carbon dioxide content.

The carbon dioxide analyzer can be generally employed to measure the content of dissolved gasses or to measure the vapor pressure of liquids. Examples of the latter application would be the measurement of the vapor pressure of petroleum and chemical products.

We claim:

1. An analyzer that determines the concentration of dissolved gas in a liquid stream which comprises:
   a. a sealed cell having an entry for liquids and an exit for liquids and means for measuring the pressure of the gas phase and means for measuring the temperature of the contents of the cell;
   b. a first valving means for diverting a portion of the liquid stream to the entry of the cell and a second valving means sealing the exit of the cell to prevent the liquid from escaping;

c. a third valving means for venting pressure from the cell;

d. an ultrasonic exciter attached to the cell capable of agitating the liquid in the cell and thereby in a short time bringing the liquid and the dissolved gas into equilibrium conditions;

e. means for sequencing the operation of the analyzer by opening the first valving means to allow liquid to enter the cell and opening the second valving means to allow liquid to leave the cell and then closing the first and second valving means to retain liquid in the cell and then opening and closing the third valving means to reduce pressure in the cell and then engaging the ultrasonic exciter for a sufficient period of time to bring the dissolved gas into equilibrium with the liquid and then measuring the pressure of the gas and the temperature of the liquid;

f. a computer which receives a signal from the means for measuring pressure and means for measuring temperature and converts these signals to provide dissolved gas content in the liquid.

2. The analyzer of claim 1 in which the liquid is a beverage and the dissolved gas is carbon dioxide.

3. The analyzer of claim 2 in which the computer is a calculating controller containing a microprocessor.

4. The analyzer of claim 2 in which the ultrasonic exciter is a piezoelectric transducer.

5. The analyzer of claim 4 in which the piezoelectric transducer is made of lead zirconate titanate.

6. The analyzer of claim 4 in which the ultrasonic exciter is driven by an ultrasonic driver of a variable frequency power oscillator.

7. The analyzer of claim 2 in which the means for measuring the pressure of the contents of the cell comprises a pressure transducer.

8. The analyzer of claim 2 in which the means for measuring the temperature of the contents of the cell is a temperature transducer.

9. The analyzer of claim 8 in which the temperature transducer uses a platinum resistance sensor.

10. The analyzer of claim 2 used in conjunction with a carbonated beverage filling line that determines the concentration of carbon dioxide of a beverage being supplied to the filling line.

11. The analyzer of claim 1 used to determine the vapor pressure of a liquid.

12. The analyzer of claim 1 used in conjunction with a chemical process for determining the concentration of gases in chemical liquids.

13. The analyzer of claim 1 used in conjunction with a petroleum process for determining the concentration of gases in petroleum.

* * * * *